United States Patent
Chadeayne

(10) Patent No.: US 12,410,129 B2
(45) Date of Patent: *Sep. 9, 2025

(54) CRYSTALLINE 5-METHOXY-N,N-DIALLYLTRYPTAMINE COMPOUNDS

(71) Applicant: CAAMTECH, INC., Issaquah, WA (US)

(72) Inventor: Andrew R. Chadeayne, Issaquah, WA (US)

(73) Assignee: CAAMTECH, INC., Issaquah, WA (US)

( * ) Notice: Subject to any disclaimer, the term of this patent is extended or adjusted under 35 U.S.C. 154(b) by 135 days.

This patent is subject to a terminal disclaimer.

(21) Appl. No.: 18/350,103

(22) Filed: Jul. 11, 2023

(65) Prior Publication Data

US 2023/0348383 A1    Nov. 2, 2023

Related U.S. Application Data

(63) Continuation of application No. 17/995,516, filed as application No. PCT/US2021/025891 on Apr. 6, 2021, now Pat. No. 11,739,060.

(60) Provisional application No. 63/132,547, filed on Dec. 31, 2020, provisional application No. 63/006,371, filed on Apr. 7, 2020.

(51) Int. Cl.
*A61K 31/4045* (2006.01)
*A61K 45/06* (2006.01)
*C07D 209/16* (2006.01)

(52) U.S. Cl.
CPC ........ *C07D 209/16* (2013.01); *A61K 31/4045* (2013.01); *A61K 45/06* (2013.01); *C07B 2200/13* (2013.01)

(58) Field of Classification Search
CPC .................................................. A61K 31/4045
USPC ....................................................... 514/415
See application file for complete search history.

(56) References Cited

U.S. PATENT DOCUMENTS

| | | | |
|---|---|---|---|
| 7,678,363 B2 | 3/2010 | Barlow et al. | |
| 11,739,060 B2* | 8/2023 | Chadeayne | C07D 209/16 514/415 |
| 2013/0210167 A1 | 8/2013 | Benchikh et al. | |
| 2018/0221396 A1 | 8/2018 | Chadeayne | |
| 2019/0142851 A1 | 5/2019 | Chadeayne | |

FOREIGN PATENT DOCUMENTS

CN    102391170 A    3/2012

OTHER PUBLICATIONS

International Search Report and Written Opinion in International Application No. PCT/US2021/025891 dated Jun. 2, 2021.
Tittarelli et al. Article entitled "Recreational Use, Analysis and Toxicity of Tryptamines" Curr Neuropharmacol.; Jan. 2015.
Andersson et al. Article entitled: "Psychoactive substances as a last resort—a qualitative study of self-treatment of migraine and cluster headaches" Harm Reduction Journal (2017).
Pham et al. "'Foxtrot' fumarate: a water-soluble salt of N,N-diallyl-5-methoxytryptamine (5-MeO-DALT)" 6 https://doi.org/10.1107/52056989021002838 Acta Cryst. (2021).
Carhart-Harris, R. L. & Goodwin, G. M. (2017). Neuropsychopharmacology, 42, 2105-2113.
Corkery, J. M., Durkin, E., Elliott, S., Schifano, F. & Ghodse, A. H. (2012). Prog. Neuro-Psychoph. 39, 259-262.
Cozzi, N. V. & Daley, P. F. (2016). Bioorg. Med. Chem. Lett. 26, 959-964.
Davis, A. K., Barrett, F. S. & Griffiths, R. R. (2020). J. Contextual Behav. Sci. 15, 39-45.
Dolomanov, 0. V., Bourhis, L. J., Gildea, R. J., Howard, J. A. K. & Puschmann, H. (2009). J. Appl. Cryst. 42, 339-341.
Erspamer, V., Vitali, T., Roseghini, M. & Cei, J.M. (1967). Biochem. Pharmaco/. 16, 1149-1164.
Etter, M. C., MacDonals, J.C. & Bernstein, J. (1990). Acta Cryst. B46, 256-262.
Sheldrick, G. M. (2015a). Acta Cryst. A71, 3-8.
Sheldrick, G. M. (2015b). Acta Cryst. C71, 3-8.
Sherwood, A. M., Claveau, R., Lancelotta, R., Kaylo, K. W. & Lenoch, K. (2020). ACS Omega, 5, 32067-32075.
Shulgin, A. T. & Shulgin, A. (2016). TIKHAL: The Continuation. Isomerdesign. Available at: http://isomerdesign.com/PiHKAL/read.php?domain=tk&id=56. Accessed Mar. 19, 2020.
Uthaug, M. V., Lancelotta, R., Szabo, A., Davis, A. K., Riba, J. & Ramaekers, J. G. (2019), Psychpharmacology 237, 773-785.
Uthaug, M. V., Lancelotta, R., van Oorsouw, K., Kuypers, K. P. C., Mason, N., Rak, J., Sulakova, A., Jurok, R., Maryska, M., Kuchar, M., Palenicek, T., Riba, J. & Ramaekers, J. G. (2019). Psychopharmacology 236, 2653-2666.
Weil, A. T. & Davis, W. (1994). J. Ethnopharmacol. 41; 1-8.
International Preliminary Report on Patentability dated Oct. 6, 2022 of PCT International Application No. PCT/US2021/025891 filed Apr. 6, 2021.
Byrn et al., "Pharmaceutical Solids: A Strategic Approach to Regulatory Considerations", Pharmaceutical Research, 12, pp. 945-954, Jul. 1995.
Post, "Treatment of Cluster Headache Symptoms using Synthetic Tryptamine N,N-Diallyl-5 Methoxytryptamine" 2014, XP093138200, https://figshare.com/articles/journal_contributionTreatment_of_Cluster_Headache_Symptoms_using_Synthetic_Tryptamine_N_N_Diallyl_5_Methoxytryptamine/1119697 [retrieved on Mar. 6, 2024].
Zhao et al., "Study on the synthesis of N,N-diallyl-5-methoxytryptamine" Huaxue Shiji—Chemical Reagents, Beijing: Huaxue Huaxue Shiji Keji Qingbao Zhongxinzhan, CN, 2006, vol. 28(5), p. 307-308, discloses the synthesis of 5-MeO-DALT.

(Continued)

*Primary Examiner* — Raymond J Henley, III
(74) *Attorney, Agent, or Firm* — RAPHAEL BELLUM PLLC

(57) ABSTRACT

The disclosure relates to 5-methoxy-N,N-diallyltryptamine ("5-MeO-DALT"), bis-(5-meth-oxy-N,N-di-allyl-tryptammonium) fumarate ("5-MeO-DALT fumarate"), and crystalline bis-(5-meth-oxy-N,N-di-allyl-tryptammonium) fumarate ("5-MeO-DALT fumarate"), compositions containing them, and the methods of treatment using them.

19 Claims, 8 Drawing Sheets

(56) References Cited

OTHER PUBLICATIONS

Nichols et al., "Classic psychedelics as therapeutics for psychiatric disorders" Handbook of the Behavioral Neurobiology of Serotonin, 2020, vol. 31, p. 959-966.
Serajuddin, "Salt formation to improve drug solubility" Advanced Drug Delivery Reviews, 2007, vol. 59(7), p. 603-616.
Chadeayne et al., "5-MeO-DALT: the freebase of N,N-diallyl-5-methoxytryptamine" IUCrData, 2020, vol. 5(4), p. x200498.
Isomerdesign (2016) "#56 5-MeO-DALT" isomerdesign.com. Retrieved from Jun. 11, 2016. URL https://web.archive.org/web/20160611030520/https://isomerdesign.com/PiHKAL/read.php?domain=tk&id56.†

* cited by examiner
† cited by third party

CRYSTALLINE 5-METHOXY-N,N-DIALLYLTRYPTAMINE COMPOUNDS

CROSS-REFERENCE TO RELATED APPLICATIONS

This application is a continuation application of U.S. application Ser. No. 17/995,516, filed on Oct. 5, 2022; which is a 371 of PCT International Application No. PCT/US2021/025891, filed on Apr. 6, 2021; which claims priority to U.S. Provisional Application No. 63/006,371 filed on Apr. 7, 2020 and to U.S. Provisional Application No. 63/132,547 filed on Dec. 31, 2020; the disclosures of which are all incorporated herein by reference.

TECHNICAL FIELD

This disclosure relates to crystalline 5-methoxy-N,N-diallyltryptamine ("5-MeO-DALT"), bis-(5-meth-oxy-N,N-di-allyl-tryptammonium) fumarate ("5-MeO-DALT fumarate"), and crystalline bis-(5-meth-oxy-N,N-di-allyl-tryptammonium) fumarate ("5-MeO-DALT fumarate"), to pharmaceutical compositions containing them and to methods of treatment/therapeutic uses of the crystalline 5-MeO-DALT, 5-MeO-DALT fumarate, or crystalline 5-MeO-DALT fumarate, and the pharmaceutical compositions.

BACKGROUND

Psychedelics have garnered a great deal of study of late as potential therapeutics for mood disorders (Davis, et al. 2020; Carhart-Harris & Goodwin, 2017). Toads in the Bufonidae family release an alkaloid toxin on their backs when they experience stress. These toads are the genesis of the urban myth of "licking toads" because the toxin contains psychedelic tryptamines. The toxin is generally known as bufotoxin, and its contents can vary greatly from species to species. Bufotoxin is a medley of different chemicals; the skin of the species *Bufo alvarius*, a desert toad of Arizona, contains a number of indolealkylamine, including bufotenine, O-methylbufotenine, and bufoviridine, among many others (Erspamer, et al. 1967).

Recent studies have shown that the psychotropic experiences of inhaling dried toad excretion and that of inhaling pure synthetic O-methylbufotenine (5-methoxy-N,N-dimethyltryptamine (5-MeO-DMT)) are markedly different (Uthaug, Lancelotta, van Oorsouw, et al. 2019; Uthaug, Lancelotta, Szabo, et al. 2019). 5-MeO-DMT is highly active at the serotonin (5-hydroxy-tryptamine, 5-HT) 2A receptor, which is the origin of its psychotropic activity. It can be administered via inhalation or injection but does not function as a psychedelic when consumed orally (Weil & Davis, 1994). A recent report described the synthesis of a water-soluble succinate salt of 5-MeO-DMT (Sherwood et al., 2020). The varied experiences suggests that the other tryptamines have significant activity in the psychedelic effects, or that they work in combination through an entourage effect. It is important to understand the pharmacology of not just 5-MeO-DMT, but all of the tryptamines in bufotoxin, and other related molecules.

5-methoxy-N,N-diallyltryptamine (5-MeO-DALT), street name Foxtrot, is a synthetic analog of O-methylbufotenine first synthesized by Alexander Shulgin in 2004 (Shulgin & Shulgin, 2016). The compound is noted for its quick onset and rapid drop-off, when compared to other psychotropic tryptamines (Corkery, et al. 2012). The pharmacology of the compound demonstrates activity at the 5-hydroxytryptamine (5-HT) receptors, particularly $5-HT_{1A}$, $5-HT_{1D}$, $5-HT_{2B}$, $5-HT_6$, and $5-HT_7$, though slightly less active at the $5-HT_{2A}$ receptor which is believed to be responsible for most psychotropic activity (Cozzi & Daley, 2016). As these molecules become more relevant in treating mood disorders, it will be important to have analytically pure, well characterized compounds, perhaps best provided by crystalline material.

Although therapeutic efficacy is the primary concern for an active pharmaceutical ingredient (API), the salt and solid-state form (i.e., the crystalline or amorphous form) of a drug candidate can be critical to its pharmacological properties, such as bioavailability, and to its development as a viable API. Recently, crystalline forms of API's have been used to alter the physicochemical properties of an API. Each crystalline form of a drug candidate can have different solid state (physical and chemical) properties. The differences in physical properties exhibited by a novel solid form of an API (such as a cocrystal or polymorph of the original therapeutic compound) affect pharmaceutical parameters such as storage stability, compressibility and density (important in formulation and product manufacturing), and solubility and dissolution rates (important factors in determining bioavailability). Because these practical physical properties are influenced by the solid-state properties of the crystalline form of the API, they can significantly impact the selection of a compound as an API, the ultimate pharmaceutical dosage form, the optimization of manufacturing processes, and absorption in the body. Moreover, finding the most adequate solid-state form for further drug development can reduce the time and the cost of that development.

Obtaining crystalline forms of an API is extremely useful in drug development. It permits better characterization of the drug candidate's chemical and physical properties. Crystalline forms often have better chemical and physical properties than the API in its amorphous state. Such crystalline forms may possess more favorable pharmaceutical and pharmacological properties or be easier to process.

SUMMARY

The disclosure relates to crystalline 5-methoxy-N,N-diallyltryptamine ("5-MeO-DALT"), bis-(5-meth-oxy-N,N-di-allyl-tryptammonium) fumarate ("5-MeO-DALT fumarate"), and crystalline bis-(5-meth-oxy-N,N-di-allyl-tryptammonium) fumarate ("5-MeO-DALT fumarate"), and to pharmaceutical compositions containing crystalline 5-MeO-DALT, 5-MeO-DALT fumarate, or crystalline 5-MeO-DALT fumarate.

In one embodiment, crystalline 5-MeO-DALT according to the disclosure is characterized by a monoclinic, $P2_1/n$ crystal system space group at a temperature of about 296 K; unit cell dimensions a=6.1444 (6) Å, b=12.8514 (13) Å, c=19.3315 (19) Å, and β=91.626 (3°); or an XRPD having peaks at 9.1, 11.4, and 21.4° 2θ±0.2° 2θ.

In one embodiment, crystalline 5-MeO-DALT fumarate according to the disclosure is characterized by a triclinic, $P^-1$ crystal system space group at a temperature of about 297 K; unit cell dimensions a=7.8791 (7) Å, b=9.2908 (7) Å, c=13.5352 (11) Å, a=108.081 (3°), p=104.365 (3°), and γ=95.903 (3°); or an XRPD having peaks at 7.2, 10.2, and 22.7° 2θ±0.2° 2θ.

The disclosure also relates to compositions comprising crystalline 5-MeO-DALT, 5-MeO-DALT fumarate, or crystalline 5-MeO-DALT fumarate according to the disclosure and to pharmaceutical compositions containing crystalline 5-MeO-DALT, 5-MeO-DALT fumarate, or crystalline 5-MeO-DALT fumarate according to the disclosure and an excipient.

The disclosure also relates to compositions comprising a combination of, as a first component, crystalline 5-MeO-DALT, 5-MeO-DALT fumarate, or crystalline 5-MeO-DALT fumarate according to the disclosure and a second component selected from (a) a serotonergic drug, (b) a purified psilocybin derivative, (c) one or two purified cannabinoids and (d) a purified terpene.

The disclosure further relates to methods of preventing or treating a physical and/or psychological disorders comprising the step of administering to a subject in need thereof an effective amount of crystalline 5-MeO-DALT, 5-MeO-DALT fumarate, or crystalline 5-MeO-DALT fumarate according to the disclosure and to pharmaceutical compositions containing crystalline 5-MeO-DALT, 5-MeO-DALT fumarate, or crystalline 5-MeO-DALT fumarate according to the disclosure, or a composition according to the disclosure.

The disclosure also relates to methods of preventing or treating inflammation and/or pain comprising the step of administering to a subject in need thereof an effective amount of crystalline 5-MeO-DALT, 5-MeO-DALT fumarate, or crystalline 5-MeO-DALT fumarate according to the disclosure and to pharmaceutical compositions containing crystalline 5-MeO-DALT, 5-MeO-DALT fumarate, or crystalline 5-MeO-DALT fumarate according to the disclosure, or a composition according to the disclosure.

DETAILED DESCRIPTION

Figure 1:
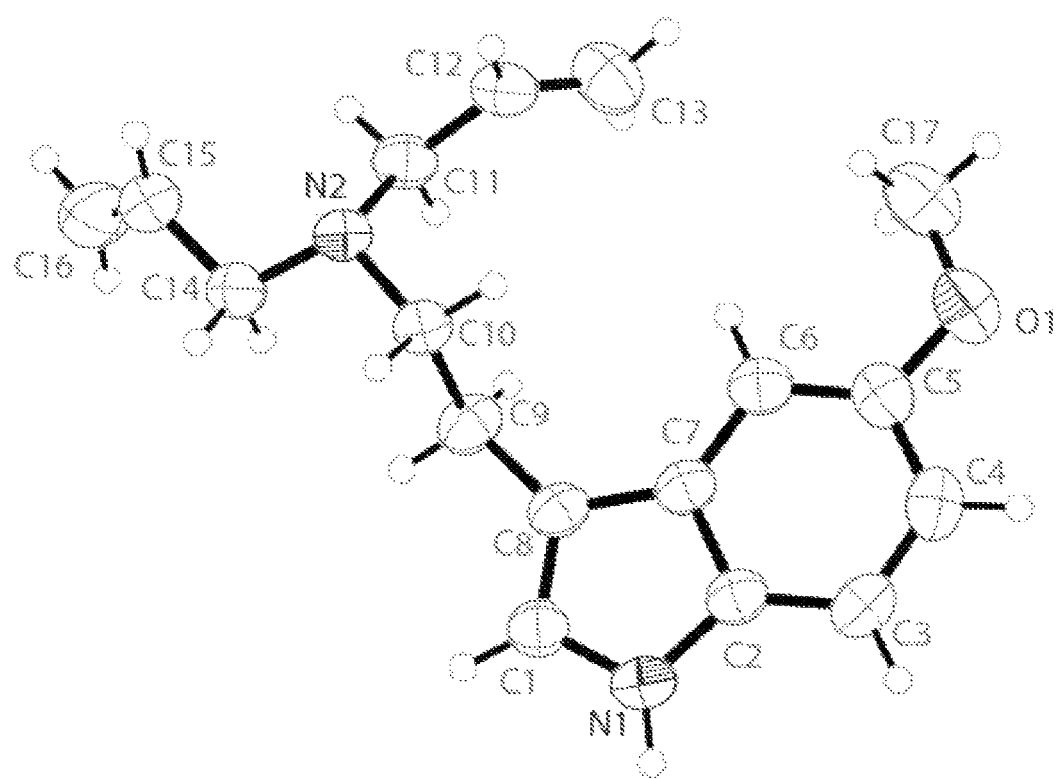
FIG. 1 shows the molecular structure of crystalline 5-MeO-DALT.

This disclosure relates to crystalline 5-methoxy-N,N-diallyltryptamine ("5-MeO-DALT"), bis-(5-meth-oxy-N,N-di-allyl-tryptammonium) fumarate ("5-MeO-DALT fumarate"), and crystalline bis-(5-meth-oxy-N,N-di-allyl-tryptammonium) fumarate ("5-MeO-DALT fumarate"), and to pharmaceutical compositions containing crystalline 5-MeO-DALT, 5-MeO-DALT fumarate, and crystalline 5-MeO-DALT fumarate according to the disclosure. The therapeutic uses of crystalline 5-MeO-DALT, 5-MeO-DALT fumarate, and crystalline 5-MeO-DALT fumarate according to the disclosure, are described below as well as compositions containing them. Crystalline 5-MeO-DALT and crystalline 5-MeO-DALT fumarate according to the disclosure, and the methods used to characterize them are described below. The novel and crystalline 5-MeO-DALT fumarate compounds of the disclosure may be used to prepare other salts, including pharmaceutically acceptable salts, by anion exchange techniques known in the art to exchange the fumarate anion for another desired anion.

5-methoxy-N,N-diallyltryptamine ("5-MeO-DALT") has the following structural formula:

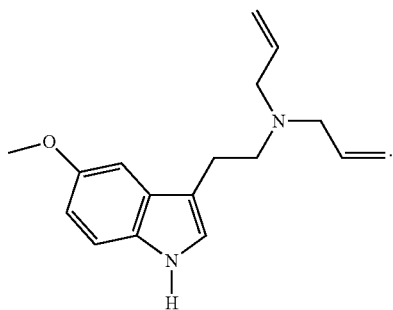 [SMILES: C=CCN(CC=C)CCc1c[nH]c2ccc(OC)cc12]

Bis-(5-meth-oxy-N,N-di-allyl-tryptammonium) fumarate ("5-MeO-DALT fumarate") has the following chemical structure:

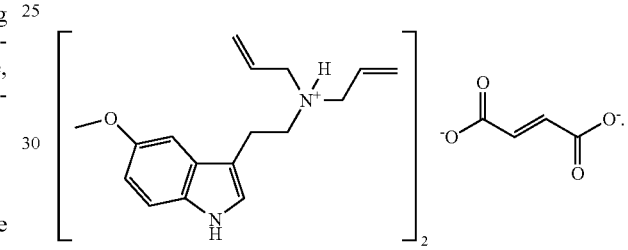

Methods of Treatment and Therapeutic Uses

In one embodiment, crystalline 5-MeO-DALT, 5-MeO-DALT fumarate, or crystalline 5-MeO-DALT fumarate according to the disclosure, and the methods and the compositions—particularly the pharmaceutical compositions—of the disclosure are used to regulate the activity of a neurotransmitter receptor by administering a therapeutically effective dose of crystalline 5-MeO-DALT, 5-MeO-DALT fumarate, or crystalline 5-MeO-DALT fumarate of the disclosure. In another embodiment, crystalline 5-MeO-DALT, 5-MeO-DALT fumarate, or crystalline 5-MeO-DALT fumarate according to the disclosure, and the methods and the compositions—particularly the pharmaceutical compositions—of the disclosure are used to treat inflammation and/or pain by administering a therapeutically effective dose of crystalline 5-MeO-DALT, 5-MeO-DALT fumarate, or crystalline 5-MeO-DALT fumarate of the disclosure.

Methods of the disclosure administer a therapeutically effective amount of crystalline 5-MeO-DALT, 5-MeO-DALT fumarate, or crystalline 5-MeO-DALT fumarate of the disclosure to prevent or treat a disease or condition, such as those discussed below for a subject in need of treatment. Crystalline 5-MeO-DALT, 5-MeO-DALT fumarate, or crystalline 5-MeO-DALT fumarate of the disclosure may be administered neat or as a composition comprising crystalline 5-MeO-DALT, 5-MeO-DALT fumarate, or crystalline 5-MeO-DALT fumarate of the disclosure as discussed below.

Crystalline 5-MeO-DALT, 5-MeO-DALT fumarate, or crystalline 5-MeO-DALT fumarate of the disclosure may be used to prevent and/or treat a psychological disorder. The disclosure provides a method for preventing and/or treating a psychological disorder by administering to a subject in need thereof a therapeutically effective amount of crystalline 5-MeO-DALT, 5-MeO-DALT fumarate, or crystalline 5-MeO-DALT fumarate of the disclosure, including the preferred embodiments discussed herein. The psychological disorder may be chosen from depression; psychotic disorder; schizophrenia; schizophreniform disorder (acute schizophrenic episode); schizoaffective disorder; bipolar I disorder (mania, manic disorder, manic-depressive psychosis); bipolar 11 disorder; major depressive disorder; major depressive disorder with psychotic feature (psychotic depression); delusional disorders (paranoia); Shared Psychotic Disorder (Shared paranoia disorder); Brief Psychotic disorder (Other and Unspecified Reactive Psychosis); Psychotic disorder not otherwise specified (Unspecified Psychosis); paranoid personality disorder; schizoid personality disorder; schizotypal personality disorder; anxiety disorder; social anxiety disorder; substance-induced anxiety disorder; selective mutism; panic disorder; panic attacks; agoraphobia; attention deficit syndrome, post-traumatic stress disorder (PTSD), premenstrual dysphoric disorder (PMDD), and premenstrual syndrome (PMS).

Crystalline 5-MeO-DALT, 5-MeO-DALT fumarate, or crystalline 5-MeO-DALT fumarate of the disclosure may be used to prevent and/or treat a brain disorder. The disclosure provides a method for preventing and/or treating a brain disorder by administering to a subject in need thereof a therapeutically effective amount of crystalline 5-MeO-DALT, 5-MeO-DALT fumarate, or crystalline 5-MeO-DALT fumarate of the disclosure, including the preferred embodiments discussed above. The brain disorder is chosen from Huntington's disease, Alzheimer's disease, dementia, and Parkinson's disease.

Crystalline 5-MeO-DALT, 5-MeO-DALT fumarate, or crystalline 5-MeO-DALT fumarate of the disclosure may be used to prevent and/or treat developmental disorders, delirium, dementia, amnestic disorders and other cognitive disorders, psychiatric disorders due to a somatic condition, drug-related disorders, schizophrenia and other psychotic disorders, mood disorders, anxiety disorders, somatoform disorders, factitious disorders, dissociative disorders, eating disorders, sleep disorders, impulse control disorders, adjustment disorders, or personality disorders. The disclosure provides a method for preventing and/or treating these disorders by administering to a subject in need thereof a therapeutically effective amount of crystalline 5-MeO-DALT, 5-MeO-DALT fumarate, or crystalline 5-MeO-DALT fumarate of the disclosure, including the preferred embodiments discussed above.

Crystalline 5-MeO-DALT, 5-MeO-DALT fumarate, or crystalline 5-MeO-DALT fumarate of the disclosure may be used to prevent and/or treat inflammation and/or pain, such as for example inflammation and/or pain associated with inflammatory skeletal or muscular diseases or conditions. The disclosure provides a method for preventing and/or treating an inflammation and/or pain by administering to a subject in need thereof a therapeutically effective amount of crystalline 5-MeO-DALT, 5-MeO-DALT fumarate, or crystalline 5-MeO-DALT fumarate of the disclosure, including the preferred embodiments discussed herein. Generally speaking, treatable "pain" includes nociceptive, neuropathic, and mix-type. A method of the disclosure may reduce or alleviate the symptoms associated with inflammation, including but not limited to treating localized manifestation of inflammation characterized by acute or chronic swelling, pain, redness, increased temperature, or loss of function in some cases. A method of the disclosure may reduce or alleviate the symptoms of pain regardless of the cause of the pain, including but not limited to reducing pain of varying severity, i.e., mild, moderate and severe pain, acute pain and chronic pain. A method of the disclosure is effective in treating joint pain, muscle pain, tendon pain, burn pain, and pain caused by inflammation such as rheumatoid arthritis. Skeletal or muscular diseases or conditions which may be treated include but are not limited to musculoskeletal sprains, musculoskeletal strains, tendinopathy, peripheral radiculopathy, osteoarthritis, joint degenerative disease, polymyalgia rheumatica, juvenile arthritis, gout, ankylosing spondylitis, psoriatic arthritis, systemic lupus erythematosus, costochondritis, tendonitis, bursitis, such as the common lateral epicondylitis (tennis elbow), medial epicondylitis (pitchers elbow) and trochanteric bursitis, temporomandibular joint syndrome, and fibromyalgia.

Compositions

The disclosure also relates to compositions comprising an effective amount of crystalline 5-MeO-DALT, 5-MeO-DALT fumarate, or crystalline 5-MeO-DALT fumarate of the disclosure, especially pharmaceutical compositions comprising a therapeutically effective amount of crystalline 5-MeO-DALT, 5-MeO-DALT fumarate, or crystalline 5-MeO-DALT fumarate of the disclosure and a pharmaceutically acceptable carrier (also known as a pharmaceutically acceptable excipient). As discussed above, crystalline 5-MeO-DALT, 5-MeO-DALT fumarate, or crystalline 5-MeO-DALT fumarate of the disclosure may be, for example, therapeutically useful to prevent and/or treat the psychological and other disorders discussed above.

A composition or a pharmaceutical composition of the disclosure may be in any form which contains crystalline 5-MeO-DALT, 5-MeO-DALT fumarate, or crystalline 5-MeO-DALT fumarate of the disclosure. The composition may be, for example, a tablet, capsule, liquid suspension, injectable, topical, or transdermal. The compositions or pharmaceutical compositions generally contain, for example, about 1% to about 99% by weight of crystalline 5-MeO-DALT, 5-MeO-DALT fumarate, or crystalline 5-MeO-DALT fumarate of the disclosure and, for example, 99% to 1% by weight of at least one suitable pharmaceutical excipient. In one embodiment, the composition may be between about 5% and about 75% by weight of crystalline 5-MeO-DALT, 5-MeO-DALT fumarate, or crystalline 5-MeO-DALT fumarate of the disclosure with the rest being at least one suitable pharmaceutical excipient or at least one other adjuvant, as discussed below.

Published US applications US 2018/0221396 A1 and US 2019/0142851 A1 disclose compositions comprising a combination of a first purified psilocybin derivative with a second purified psilocybin derivative, with one or two purified cannabinoids or with a purified terpene. Various ratios of these components in the composition are also disclosed. The disclosures of US 2018/0221396 A1 and US 2019/0142851 A1 are incorporated herein by reference. According to this disclosure, crystalline 5-MeO-DALT, 5-MeO-DALT fumarate, or crystalline 5-MeO-DALT fumarate of the disclosure may be used as the "first purified psilocybin derivative" in the compositions described in US 2018/0221396 A1 and US 2019/0142851 A1. Accordingly, this disclosure provides a composition comprising as a first component: crystalline 5-MeO-DALT, 5-MeO-DALT fumarate, or crystalline 5-MeO-DALT fumarate of the disclosure; and as a second component selected from (a) a serotonergic drug, (b) a purified psilocybin derivative, (c) one or two purified cannabinoids and (d) a purified terpene; with the rest being at least one suitable pharmaceutical excipient or at least one other adjuvant, as discussed below. Such a composition may be a pharmaceutical composition wherein the components are present individually in therapeutically effective amounts or by combination in a therapeutically effective amount to treat a disease, disorder, or condition as described herein. A serotonergic drug refers to a compound that binds to, blocks, or otherwise influences (e.g., via an allosteric reaction) activity at a serotonin receptor as described in paragraphs [0245]-[0253] of US 2018/0221396 A1 and [0305]-[0311] US 2019/0142851 A1 as well as the disclosed preferred embodiments, incorporated here by reference. Exemplary psilocybin derivatives include but are not limited to psilocybin itself and the psilocybin derivates described in paragraphs [0081]-[0109] of US 2018/0221396 A1 and [082]-[0110] US 2019/0142851 A1 as well as the disclosed preferred embodiments. Exemplary cannabinoids include but are not limited to the cannabinoids described in paragraphs [0111]-[0159] of US 2018/0221396 A1 and [0112]-[0160] US 2019/0142851 A1 as well as the disclosed preferred embodiments. Exemplary terpenes include but are not limited to the terpenes described in paragraphs [0160]-[0238] of US 2018/0221396 A1 and [0161]-[0300] US 2019/0142851 A1 as well as the disclosed preferred embodiments.

A pharmaceutical formulation of the disclosure may comprise, consist essentially of, or consist of (a) crystalline 5-MeO-DALT, 5-MeO-DALT fumarate, or crystalline 5-MeO-DALT fumarate of the disclosure and (b) a second active compound selected from a serotonergic drug, a purified psilocybin derivative, a purified cannabinoid, or a purified terpene and (c) a pharmaceutically acceptable excipient. Crystalline 5-MeO-DALT, 5-MeO-DALT fumarate, or crystalline 5-MeO-DALT fumarate of the disclosure and the second active compound are each present in a therapeutically effective amount using a purposefully engineered and unnaturally occurring molar ratios. Exemplary molar ratios of crystalline 5-MeO-DALT, 5-MeO-DALT fumarate, or crystalline 5-MeO-DALT fumarate of the disclosure to the second active compound in a composition of the disclosure include but are not limited to from about 0.1:100 to about 100:0.1, from about 1:100 to about 100:1, from about 1:50 to about 50:1, from about 1:25 to about 25:1, from about 1:20 to about 20:1, from about 1:10 to about 10:1, from about 1:5 to about 5:1, from about 1:2 to about 2:1 or may be about 1:1.

A pharmaceutical formulation of the disclosure may comprise a composition of the disclosure and a serotonergic drug, a purified psilocybin derivative, a purified cannabinoid, or a purified terpene, each present in a therapeutically effective amount using a purposefully engineered and unnaturally occurring molar ratios. Published US applications US 2018/0221396 A1 and US 2019/0142851 A1 disclose compositions comprising a combination of a purified psilocybin derivative with a second purified psilocybin derivative, with one or two purified cannabinoids or with a purified terpene. The disclosures of US 2018/0221396 A1 and US 2019/0142851 A1 are incorporated herein by reference. According to this disclosure a composition containing crystalline 5-MeO-DALT, 5-MeO-DALT fumarate, or crystalline 5-MeO-DALT fumarate as discussed above may be used in place of a "purified psilocybin derivative" in the compositions described in US 2018/0221396 A1 and US 2019/0142851 A1. Accordingly, the disclosure provides a pharmaceutical formulation comprising as (a) crystalline 5-MeO-DALT, 5-MeO-DALT fumarate, or crystalline 5-MeO-DALT fumarate of the disclosure and as a second component selected from (a) a purified psilocybin derivative, (b) one or two purified cannabinoids and (c) a purified terpene; with the rest being at least one suitable pharmaceutical excipient or at least one other adjuvant, as discussed below. Such a composition may be a pharmaceutical composition wherein the components are present individually in therapeutic effective amounts or by combination in a therapeutically effective amount to treat a disease, disorder, or condition as described herein.

A serotonergic drug refers to a compound that binds to, blocks, or otherwise influences (e.g., via an allosteric reaction) activity at a serotonin receptor as described in paragraphs [0245]-[0253] of US 2018/0221396 A1 and [0305]-[0311] US 2019/0142851 A1 as well as the disclosed preferred embodiments, incorporated here by reference. Some exemplary serotonergic drugs include the following molecules: 6-Allyl-N,N-diethyl-NL, N,N-Dibutyl-T, N,N-Diethyl-T, N,N-Diisopropyl-T, 5-Methyoxy-alpha-methyl-T, N,N-Dimethyl-T, 2,alpha-Dimethyl-T, alpha,N-Dimethyl-T, N,N-Dipropyl-T, N-Ethyl-N-isopropyl-T, alpha-Ethyl-T, 6,N,N-Triethyl-NL, 3,4-Dihydro-7-methoxy-1-methyl-C, 7-Methyoxy-1-methyl-C, N,N-Dibutyl-4-hydroxy-T, N,N-Diethyl-4-hydroxy-T, N,N-Diisopropyl-4-hydroxy-T, N,N-Dimethyl-4-hydroxy-T, N,N-Dimethyl-5-hydroxy-T, N, N-Dipropyl-4-hydroxy-T, N-Ethyl-4-hydroxy-N-methyl-T, 4-Hydroxy-N-isopropyl-N-methyl-T, 4-Hydroxy-N-methyl-N-propyl-T, 4-Hydroxy-N,N-tetramethylene-T Ibogaine, N,N-Diethyl-L, N-Butyl-N-methyl-T, N,N-Diisopropyl-4,5-methylenedioxy-T, N,N-Diisopropyl-5,6-methylenedioxy-T, N,N-Dimethyl-4,5-methylenedioxy-T, N,N-Dimethyl-5,6-methylenedioxy-T, N-Isopropyl-N-methyl-5,6-methylenedioxy-T, N,N-Diethyl-2-methyl-T, 2,N,N-Trimethyl-T, N-Acetyl-5-methoxy-T, N,N-Diethyl-5-methoxy-T, N,N-Diisopropyl-5-methoxy-T, 5-Methoxy-N,N-dimethyl-T, N-Isopropyl-4-methoxy-N-methyl-T, N-Isopropyl-5-methoxy-N-methyl-T, 5,6-Dimethoxy-N-isopropyl-N-methyl-T, 5-Methoxy-N-methyl-T, 5-Methoxy-N,N-tetramethylene-T, 6-Methoxy-1-methyl-1,2,3,4-tetrahydro-C, 5-Methoxy-2,N,N-trimethyl-T, N,N-Dimethyl-5-methylthio-T, N-Isopropyl-N-methyl-T, alpha-Methyl-T, N-Ethyl-T, N-Methyl-T, 6-Propyl-N L, N,N-Tetramethylene-T, Tryptamine, and 7-Methoxy-1-methyl-1,2,3,4-tetrahydro-C, alpha,N-Dimethyl-5-methoxy-T. For additional information regarding these compounds See Shulgin, A. T., & Shulgin, A. (2016). Tihkal: The Continuation. Berkeley, Calif.: Transform Press. In one embodiment, a serotonergic drug is chosen from alprazolam, amphetamine, aripiprazole, azapirone, a barbiturate, bromazepam, bupropion, buspirone, a cannabinoid, chlordiazepoxide, citalopram, clonazepam, clorazepate, dextromethorphan, diazepam, duloxetine, escitalopram, fluoxetine, flurazepam, fluvoxamine, lorazepam, lysergic acid diethylamide, lysergamide, 3,4-methylenedioxymethamphetamine, milnacipran, mirtazapine, naratriptan, paroxetine, pethidine, phenethylamine, psicaine, oxazepam, reboxetine, serenic, serotonin, sertraline, temazepam, tramadol, triazolam, a tryptamine, venlafaxine, vortioxetine, and/or derivatives thereof. In a preferred embodiment, the serotonergic drug is 3,4-methylenedioxymethamphetamine.

Exemplary psilocybin derivatives include but are not limited to psilocybin itself and the psilocybin derivates described in paragraphs [0081]-[0109] of US 2018/0221396 A1 and [082]-[0110] US 2019/0142851 A1 as well as the disclosed preferred embodiments, incorporated here by reference. In one embodiment, the compositions disclosed herein comprise one or more purified psilocybin derivatives chosen from: [3-(2-Dimethylaminoethyl)-1H-indol-4-yl]dihydrogen phosphate, 4-hydroxytryptamine, 4-hydroxy-N,N- dimethyltryptamine, [3-(2-methylaminoethyl)-1H-indol-4-yl]dihydrogen phosphate, 4-hydroxy-N-methyltryptamine, [3-(aminoethyl)-1H-indol-4-yl]dihydrogen phosphate, [3-(2-trimethylaminoethyl)-1H-indol-4-yl]dihydrogen phosphate, and 4-hydroxy-N,N,N-trimethyltryptamine.

Exemplary cannabinoids include but are not limited to the cannabinoids described in paragraphs [0111]-[0159] of US 2018/0221396 A1 and [0112]-[0160] US 2019/0142851 A1 as well as the disclosed preferred embodiments, incorporated here by reference. Examples of cannabinoids within the context of this disclosure include the following molecules: Cannabichromene (CBC), Cannabichromenic acid (CBCA), Cannabichromevarin (CBCV), Cannabichromevarinic acid (CBCVA), Cannabicyclol (CBL), Cannabicyclolic acid (CBLA), Cannabicyclovarin (CBLV), Cannabidiol (CBD), Cannabidiol monomethylether (CBDM), Cannabidiolic acid (CBDA), Cannabidiorcol (CBD-C1), Cannabidivarin (CBDV), Cannabidivarinic acid (CBDVA), Cannabielsoic acid B (CBEA-B), Cannabielsoin (CBE), Cannabielsoin acid A (CBEA-A), Cannabigerol (CBG), Cannabigerol monomethylether (CBGM), Cannabigerolic acid (CBGA), Cannabigerolic acid monomethylether (CBGAM), Cannabigerovarin (CBGV), Cannabigerovarinic acid (CBGVA), Cannabinodiol (CBND), Cannabidivarin (CBDV), Cannabinol (CBN), Cannabinol methylether (CBNM), Cannabinol-C2 (CBN-C2), Cannabinol-C4 (CBN-C4), Cannabinolic acid (CBNA), Cannabiorcool (CBN-C1), Cannabivarin (CBV), Cannabitriol (CBT), Cannabitriolvarin (CBTV), 10-Ethoxy-9-hydroxy-delta-6a-tetrahydrocannabinol, Cannabicitran (CBT), Cannabiripsol (CBR), 8,9-Dihydroxy-delta-6a-tetrahydrocannabinol, Delta-8-tetrahydrocannabinol (A8-THC), Delta-8-tetrahydrocannabinolic acid (A8-THCA), Delta-9-tetrahydrocannabinol (THC), Delta-9-tetrahydrocannabinol-C4 (THC-C4), Delta-9-tetrahydrocannabinolic acid A (THCA-A), Delta-9-tetrahydrocannabinolic acid B (THCA-B), Delta-9-tetrahydrocannabinolic acid-C4 (THCA-C4), Delta-9-tetrahydrocannabiorcol (THC-C1), Delta-9-tetrahydrocannabiorcolic acid (THCA-C1), Delta-9-tetrahydrocannabivarin (THCV), Delta-9-tetrahydrocannabivarinic acid (THCVA), 10-Oxo-delta-6a-tetrahydrocannabinol (OTHC), Cannabichromanon (CBCF), Cannabifuran (CBF), Cannabiglendol, Delta-9-cis-tetrahydrocannabinol (cis-THC), Tryhydroxy-delta-9-tetrahydrocannabinol (triOH-THC), Dehydrocannabifuran (DCBF), and 3,4,5,6-Tetrahydro-7-hydroxy-alpha-alpha-2-trimethyl-9-n-propyl-2,6-metha-no-2H-1-benzoxocin-5-methanol. In one embodiment, the purified cannabinoid is chosen from THC, THCA, THCV, THCVA, CBC, CBCA, CBCV, CBCVA, CBD, CBDA, CBDV, CBDVA, CBG, CBGA, CBGV, or CBGVA.

Exemplary terpenes include but are not limited to the terpenes described in paragraphs [0160]-[0238] of US 2018/0221396 A1 and [0161]-[0300] US 2019/0142851 A1 as well as the disclosed preferred embodiments, incorporated here by reference. In one embodiment, a purified terpene is chosen from acetanisole, acetyl cedrene, anethole, anisole, benzaldehyde, bornyl acetate, borneol, cadinene, cafestol, caffeic acid, camphene, camphor, capsaicin, carene, carotene, carvacrol, carvone, caryophyllene, caryophyllene, caryophyllene oxide, cedrene, cedrene epoxide, cecanal, cedrol, cembrene, cinnamaldehyde, cinnamic acid, citronellal, citronellol, cymene, eicosane, elemene, estragole, ethyl acetate, ethyl cinnamate, ethyl maltol, eucalyptol/1,8-cineole, eudesmol, eugenol, euphol, farnesene, farnesol, fenchone, geraniol, geranyl acetate, guaia-1(10),11-diene, guaiacol, guaiol, guaiene, gurjunene, herniarin, hexanaldehyde, hexanoic acid, humulene, ionone, ipsdienol, isoamyl acetate, isoamyl alcohol, isoamyl formate, isoborneol, isomyrcenol, isoprene, isopulegol, isovaleric acid, lavandulol, limonene, gamma-linolenic acid, linalool, longifolene, lycopene, menthol, methyl butyrate, 3-mercapto-2-methylpentanal, beta-mercaptoethanol, mercaptoacetic acid, methyl salicylate, methylbutenol, methyl-2-methylvalerate, methyl thiobutyrate, myrcene, gamma-muurolene, nepetalactone, nerol, nerolidol, neryl acetate, nonanaldehyde, nonanoic acid, ocimene, octanal, octanoic acid, pentyl butyrate, phellandrene, phenylacetaldehyde, phenylacetic acid, phenylethanethiol, phytol, pinene, propanethiol, pristimerin, pulegone, retinol, rutin, sabinene, squalene, taxadiene, terpineol, terpine-4-ol, terpinolene, thujone, thymol, umbelliferone, undecanal, verdoxan, or vanillin. In one embodiment, a purified terpene is chosen from bornyl acetate, alpha-bisabolol, borneol, camphene, camphor, carene, caryophyllene, cedrene, cymene, elemene, eucalyptol, eudesmol, farnesene, fenchol, geraniol, guaiacol, humulene, isoborneol, limonene, linalool, menthol, myrcene, nerolidol, ocimene, phellandrene, phytol, pinene, pulegone, sabinene, terpineol, terpinolene, or valencene.

Exemplary compositions of crystalline 5-MeO-DALT, 5-MeO-DALT fumarate, or crystalline 5-MeO-DALT fumarate of the disclosure and a second compound selected from a serotonergic drug, a purified psilocybin derivative, a purified cannabinoid, or a purified terpene in exemplary molar ratios are shown in Table 1.

TABLE 1

| Second Compound | Molar ratio of crystalline 5-MeO-DALT, 5-MeO-DALT fumarate, or crystalline 5-MeO-DALT fumarate: second compound | Molar ratio of crystalline 5-MeO-DALT, 5-MeO-DALT fumarate, or crystalline 5-MeO-DALT fumarate: second compound | Molar ratio of crystalline 5-MeO-DALT, 5-MeO-DALT fumarate, or crystalline 5-MeO-DALT fumarate: second compound |
|---|---|---|---|
| 3,4-methylenedioxymethamphetamine | About 1:100 to about 100:1 | About 1:25 to about 25:1 | About 1:5 to about 5:1 |
| Citalopram | About 1:100 to about 100:1 | About 1:25 to about 25:1 | About 1:5 to about 5:1 |
| Escitalopram | About 1:100 to about 100:1 | About 1:25 to about 25:1 | About 1:5 to about 5:1 |
| Fluoxetine | About 1:100 to about 100:1 | About 1:25 to about 25:1 | About 1:5 to about 5:1 |
| Paroxetine | About 1:100 to about 100:1 | About 1:25 to about 25:1 | About 1:5 to about 5:1 |
| Sertraline | About 1:100 to about 100:1 | About 1:25 to about 25:1 | About 1:5 to about 5:1 |

TABLE 1-continued

| Second Compound | Molar ratio of crystalline 5-MeO-DALT, 5-MeO-DALT fumarate, or crystalline 5-MeO-DALT fumarate: second compound | Molar ratio of crystalline 5-MeO-DALT, 5-MeO-DALT fumarate, or crystalline 5-MeO-DALT fumarate: second compound | Molar ratio of crystalline 5-MeO-DALT, 5-MeO-DALT fumarate, or crystalline 5-MeO-DALT fumarate: second compound |
|---|---|---|---|
| [3-(2-Dimethylaminoethyl)-1H-indol-4-yl] dihydrogen phosphate | About 1:100 to about 100:1 | About 1:25 to about 25:1 | About 1:5 to about 5:1 |
| 4-hydroxytryptamine | About 1:100 to about 100:1 | About 1:25 to about 25:1 | About 1:5 to about 5:1 |
| 4-hydroxy-N,N-dimethyltryptamine | About 1:100 to about 100:1 | About 1:25 to about 25:1 | About 1:5 to about 5:1 |
| [3-(2-methylaminoethyl)-1H-indol-4-yl] dihydrogen phosphate | About 1:100 to about 100:1 | About 1:25 to about 25:1 | About 1:5 to about 5:1 |
| 4-hydroxy-N-methyltryptamine | About 1:100 to about 100:1 | About 1:25 to about 25:1 | About 1:5 to about 5:1 |
| [3-(aminoethyl)-1H-indol-4-yl] dihydrogen phosphate | About 1:100 to about 100:1 | About 1:25 to about 25:1 | About 1:5 to about 5:1 |
| [3-(2-trimethylaminoethyl)-1H-indol-4-yl] dihydrogen phosphate | About 1:100 to about 100:1 | About 1:25 to about 25:1 | About 1:5 to about 5:1 |
| 4-hydroxy-N,N,N-trimethyltryptamine | About 1:100 to about 100:1 | About 1:25 to about 25:1 | About 1:5 to about 5:1 |
| THC | About 1:100 to about 100:1 | About 1:25 to about 25:1 | About 1:5 to about 5:1 |
| CBC | About 1:100 to about 100:1 | About 1:25 to about 25:1 | About 1:5 to about 5:1 |
| CBD | About 1:100 to about 100:1 | About 1:25 to about 25:1 | About 1:5 to about 5:1 |
| CBG | About 1:100 to about 100:1 | About 1:25 to about 25:1 | About 1:5 to about 5:1 |
| Myrcene | About 1:100 to about 100:1 | About 1:25 to about 25:1 | About 1:5 to about 5:1 |
| Pinene | About 1:100 to about 100:1 | About 1:25 to about 25:1 | About 1:5 to about 5:1 |
| Caryophyllene | About 1:100 to about 100:1 | About 1:25 to about 25:1 | About 1:5 to about 5:1 |
| Limonene | About 1:100 to about 100:1 | About 1:25 to about 25:1 | About 1:5 to about 5:1 |
| Humulene | About 1:100 to about 100:1 | About 1:25 to about 25:1 | About 1:5 to about 5:1 |
| Linalool | About 1:100 to about 100:1 | About 1:25 to about 25:1 | About 1:5 to about 5:1 |

Exemplary pharmaceutical compositions of crystalline 5-MeO-DALT, 5-MeO-DALT fumarate, or crystalline 5-MeO-DALT fumarate of the disclosure and a second compound selected from a serotonergic drug, a purified psilocybin derivative, a purified cannabinoid, or a purified terpene and an excipient with exemplary molar ratios of crystalline 5-MeO-DALT, 5-MeO-DALT fumarate, or crystalline 5-MeO-DALT fumarate of the disclosure to the second compound are shown in Table 2.

TABLE 2

| Second Compound | Molar ratio crystalline 5-MeO-DALT, 5-MeO-DALT fumarate, or crystalline 5-MeO-DALT fumarate: second compound | Molar ratio of crystalline 5-MeO-DALT, 5-MeO-DALT fumarate, or crystalline 5-MeO-DALT fumarate: second compound | Molar ratio of crystalline 5-MeO-DALT, 5-MeO-DALT fumarate, or crystalline 5-MeO-DALT fumarate: second compound |
|---|---|---|---|
| 3,4-methylenedioxymethamphetamine | About 1:100 to about 100:1 | About 1:25 to about 25:1 | About 1:5 to about 5:1 |
| Citalopram | About 1:100 to about 100:1 | About 1:25 to about 25:1 | About 1:5 to about 5:1 |
| Escitalopram | About 1:100 to about 100:1 | About 1:25 to about 25:1 | About 1:5 to about 5:1 |
| Fluoxetine | About 1:100 to about 100:1 | About 1:25 to about 25:1 | About 1:5 to about 5:1 |
| Paroxetine | About 1:100 to about 100:1 | About 1:25 to about 25:1 | About 1:5 to about 5:1 |

TABLE 2-continued

| Second Compound | Molar ratio of crystalline 5-MeO-DALT, 5-MeO-DALT fumarate, or crystalline 5-MeO-DALT fumarate: second compound | Molar ratio of crystalline 5-MeO-DALT, 5-MeO-DALT fumarate, or crystalline 5-MeO-DALT fumarate: second compound | Molar ratio of crystalline 5-MeO-DALT, 5-MeO-DALT fumarate, or crystalline 5-MeO-DALT fumarate: second compound |
|---|---|---|---|
| Sertraline | About 1:100 to about 100:1 | About 1:25 to about 25:1 | About 1:5 to about 5:1 |
| [3-(2-Dimethylaminoethyl)-1H-indol-4-yl] dihydrogen phosphate | About 1:100 to about 100:1 | About 1:25 to about 25:1 | About 1:5 to about 5:1 |
| 4-hydroxytryptamine | About 1:100 to about 100:1 | About 1:25 to about 25:1 | About 1:5 to about 5:1 |
| 4-hydroxy-N,N-dimethyltryptamine | About 1:100 to about 100:1 | About 1:25 to about 25:1 | About 1:5 to about 5:1 |
| [3-(2-methylaminoethyl)-1H-indol-4-yl] dihydrogen phosphate | About 1:100 to about 100:1 | About 1:25 to about 25:1 | About 1:5 to about 5:1 |
| 4-hydroxy-N-methyltryptamine | About 1:100 to about 100:1 | About 1:25 to about 25:1 | About 1:5 to about 5:1 |
| [3-(aminoethyl)-1H-indol-4-yl] dihydrogen phosphate | About 1:100 to about 100:1 | About 1:25 to about 25:1 | About 1:5 to about 5:1 |
| [3-(2-trimethylaminoethyl)-1H-indol-4-yl] dihydrogen phosphate | About 1:100 to about 100:1 | About 1:25 to about 25:1 | About 1:5 to about 5:1 |
| 4-hydroxy-N,N,N-trimethyltryptamine | About 1:100 to about 100:1 | About 1:25 to about 25:1 | About 1:5 to about 5:1 |
| THC | About 1:100 to about 100:1 | About 1:25 to about 25:1 | About 1:5 to about 5:1 |
| CBC | About 1:100 to about 100:1 | About 1:25 to about 25:1 | About 1:5 to about 5:1 |
| CBD | About 1:100 to about 100:1 | About 1:25 to about 25:1 | About 1:5 to about 5:1 |
| CBG | About 1:100 to about 100:1 | About 1:25 to about 25:1 | About 1:5 to about 5:1 |
| Myrcene | About 1:100 to about 100:1 | About 1:25 to about 25:1 | About 1:5 to about 5:1 |
| Pinene | About 1:100 to about 100:1 | About 1:25 to about 25:1 | About 1:5 to about 5:1 |
| Caryophyllene | About 1:100 to about 100:1 | About 1:25 to about 25:1 | About 1:5 to about 5:1 |
| Limonene | About 1:100 to about 100:1 | About 1:25 to about 25:1 | About 1:5 to about 5:1 |
| Humulene | About 1:100 to about 100:1 | About 1:25 to about 25:1 | About 1:5 to about 5:1 |
| Linalool | About 1:100 to about 100:1 | About 1:25 to about 25:1 | About 1:5 to about 5:1 |

An "effective amount" or a "therapeutically effective amount" of crystalline 5-MeO-DALT, 5-MeO-DALT fumarate, or crystalline 5-MeO-DALT fumarate according to the disclosure is generally in the range of about 0.1 to about 100 mg daily (oral dose), of about 0.1 to about 50 mg daily (oral dose) of about 0.25 to about 25 mg daily (oral dose), of about 0.1 to about 5 mg daily (oral dose) or of about 0.5 to about 2.5 mg daily (oral dose). The actual amount required for treatment of any particular patient may depend upon a variety of factors including, for example, the disease being treated and its severity; the specific pharmaceutical composition employed; the age, body weight, general health, sex, and diet of the patient; the mode of administration; the time of administration; the route of administration; and the rate of excretion; the duration of the treatment; any drugs used in combination or coincidental with the specific compound employed; and other such factors well known in the medical arts. These factors are discussed in Goodman and Gilman's "The Pharmacological Basis of Therapeutics," Tenth Edition, A. Gilman, J. Hardman and L. Limbird, eds., McGraw-Hill Press, 155-173 (2001), which is incorporated herein by reference. Crystalline 5-MeO-DALT, 5-MeO-DALT fumarate, or crystalline 5-MeO-DALT fumarate according to the disclosure, compositions and pharmaceutical compositions containing them may be used in combination with other agents that are generally administered to a patient being treated for psychological and other disorders discussed above. They may also be co-formulated with one or more of such agents in a single pharmaceutical composition.

Depending on the type of composition or pharmaceutical composition, the excipient or pharmaceutically acceptable carrier may be chosen from any one or a combination of carriers known in the art. The choice of the pharmaceutically acceptable carrier depends upon the pharmaceutical form and the desired method of administration to be used. Preferred carriers include those that do not substantially alter crystalline 5-MeO-DALT, 5-MeO-DALT fumarate, or crystalline 5-MeO-DALT fumarate of the disclosure or produce undesirable biological effects or otherwise interact in a deleterious manner with any other component(s) of the pharmaceutical composition.

The compositions or pharmaceutical compositions of the disclosure may be prepared by methods known in the pharmaceutical formulation art, for example, see Remington's Pharmaceutical Sciences, 18th Ed., (Mack Publishing Company, Easton, Pa., 1990), which is incorporated herein by reference. In a solid dosage form, crystalline 5-MeO-DALT, 5-MeO-DALT fumarate, or crystalline 5-MeO-DALT fumarate of the disclosure may be admixed with at least one pharmaceutically acceptable excipient such as, for example, sodium citrate or dicalcium phosphate or (a) fillers or extenders, such as, for example, starches, lactose, sucrose, glucose, mannitol, and silicic acid, (b) binders, such as, for example, cellulose derivatives, starch, alignates, gelatin, polyvinylpyrrolidone, sucrose, and gum acacia, (c) humectants, such as, for example, glycerol, (d) disintegrating agents, such as, for example, agar-agar, calcium carbonate, potato or tapioca starch, alginic acid, croscarmellose sodium, complex silicates, and sodium carbonate, (e) solution retarders, such as, for example, paraffin, (f) absorption accelerators, such as, for example, quaternary ammonium compounds, (g) wetting agents, such as, for example, cetyl alcohol, and glycerol monostearate, magnesium stearate and the like (h) adsorbents, such as, for example, kaolin and bentonite, and (i) lubricants, such as, for example, talc, calcium stearate, magnesium stearate, solid polyethylene glycols, sodium lauryl sulfate, or mixtures thereof. In the case of capsules, tablets, and pills, the dosage forms may also comprise buffering agents.

Excipients or pharmaceutically acceptable adjuvants known in the formulation art may also be used in the pharmaceutical compositions of the disclosure. These include, but are not limited to, preserving, wetting, suspending, sweetening, flavoring, perfuming, emulsifying, and dispensing agents. Prevention of the action of microorganisms may be ensured by inclusion of various antibacterial and antifungal agents, for example, parabens, chlorobutanol, phenol, sorbic acid, and the like. It may also be desirable to include isotonic agents, for example, sugars, sodium chloride, and the like. If desired, a composition or a pharmaceutical composition of the disclosure may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

Solid dosage forms as described above may be prepared with coatings and shells, such as enteric coatings and others well known in the art. They may contain pacifying agents and can also be of such composition that they release the active compound or compounds in a certain part of the intestinal tract in a delayed manner. Non-limiting examples of embedded compositions that may be used are polymeric substances and waxes. The active compounds may also be in microencapsulated form, if appropriate, with one or more of the above-mentioned excipients.

Suspensions, in addition to the active compounds, may contain suspending agents, such as, for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Solid dosage forms for oral administration, which includes capsules, tablets, pills, powders, and granules, may be used. In such solid dosage forms, the active compound may be mixed with at least one inert, pharmaceutically acceptable excipient (also known as a pharmaceutically acceptable carrier).

Administration of crystalline 5-MeO-DALT, 5-MeO-DALT fumarate, or crystalline 5-MeO-DALT fumarate of the disclosure in pure form, with a permeation enhancer, with stabilizers (e.g. antioxidants), or in an appropriate pharmaceutical composition may be carried out via any of the accepted modes of administration or agents for serving similar utilities. Thus, administration may be, for example, orally, buccally, nasally, parenterally (intravenous, intramuscular, or subcutaneous), topically, transdermally, intravaginally, intravesically, or intrasystemically, in the form of solid, semi-solid, lyophilized powder, liquid dosage forms, such as, for example, tablets, suppositories, pills, soft elastic and hard gelatin capsules, powders, suspensions, or aerosols, or the like, such as, for example, in unit dosage forms suitable for simple administration of precise dosages. One route of administration may be oral administration, using a convenient daily dosage regimen that can be adjusted according to the degree of severity of the disease-state to be treated.

EXAMPLES

The preparation of crystalline 5-methoxy-N,N-diallyl-tryptamine ("5-MeO-DALT") and crystalline bis-(5-methoxy-N,N-di-allyl-tryptammonium) fumarate ("5-MeO-DALT fumarate") are described below.

Example 1: Synthesis and Crystallization of Crystalline 5-MeO-DALT

Slow evaporation of an acetone solution of a commercial sample (The Indole Shop) of 5-MeO-DALT freebase resulted in the formation of crystals of 5-methoxy-N,N-diallyltryptamine suitable for X-ray analysis.

Single crystal data, data collection, and structure refinement details are summarized in Table 3.

TABLE 3

| | 5-MeO-DALT |
|---|---|
| Chemical formula | $C_{17}H_{22}N_2O$ |
| $M_r$ | 270.36 |
| Crystal system, space group | Monoclinic, $P2_1/n$ |
| Temperature (K) | 296 |
| a, b, c (Å) | 6.1444 (6), 12.8514 (13), 19.3315 (19) |
| β (°) | 91.626 (3) |
| V (Å$^3$) | 1525.9 (3) |
| Z | 4 |
| Radiation type | Mo Kα |
| μ (mm$^{-1}$) | 0.07 |
| Crystal size (mm) | 0.3 × 0.1 × 0.03 |
| F(000) | 584 |
| $D_x$ (Mg m$^{-3}$) | 1.177 |
| λ (Å) | 0.71073 |
| θ (°) | 3.2-24.5 |

TABLE 3-continued

| | 5-MeO-DALT |
|---|---|
| PLATE | Colourless |
| Diffractometer | Bruker D8 Venture CMOS |
| Absorption correction | Absorption correction: multi-scan SADABS (Bruker, 2018) was used for absorption correction. wR2(int) was 0.0650 before and 0.0579 after correction. The Ratio of minimum to maximum transmission is 0.9312. The λ/2 correction factor is not present. |
| $T_{min}$, $T_{max}$ | 0.694, 0.745 |
| No. of measured, independent and observed [I > 2σ(I)] reflections | 45375, 2810, 2145 |
| $R_{int}$ | 0.068 |
| $\theta_{max}$, $\theta_{min}$ (°) | 25.5, 3.2 |
| h | −7→7 |
| k | −15→15 |
| l | −23→23 |
| Refinement | $F^2$ |
| Least-squares matrix | Full |
| $R[F^2 > 2\sigma(F^2)]$, $wR(F^2)$, S | 0.041, 0.106, 1.05 |
| No. of reflections | 2810 |
| No. of parameters | 186 |
| No. of restraints | 1 |
| Hydrogen site location | Mixed |
| H-atom treatment | H atoms treated by a mixture of independent and constrained refinement |
| w | $1/[\sigma^2(F_o^2) + (0.0421P)^2 + 0.3975P]$ where $P = (F_o^2 + 2F_c^2)/3$ |
| $(\Delta/\sigma)_{max}$ | <0.001 |
| $\Delta\rho_{max}$, $\Delta\rho_{min}$ (e Å$^{-3}$) | 0.15, −0.13 |
| Extinction Correction | SHELXL2018 (Sheldrick, 2015b), $Fc^* = kFc[1 + 0.001xFc^2\lambda^3/\sin(2\theta)]^{-1/4}$ |
| Extinction Coefficient | 0.36 (4) |

Data collection: APEX3 (Bruker, 2018); cell refinement: SAINT (Bruker, 2018); data reduction: SAINT (Bruker, 2018); program(s) used to solve structure: SHELXT2014 (Sheldrick, 2015a); program(s) used to refine structure: SHELXL2018 (Sheldrick, 2015b); molecular graphics: Olex2 (Dolomanov et al., 2009); software used to prepare material for publication: Olex2 (Dolomanov et al., 2009).

Figure 2:
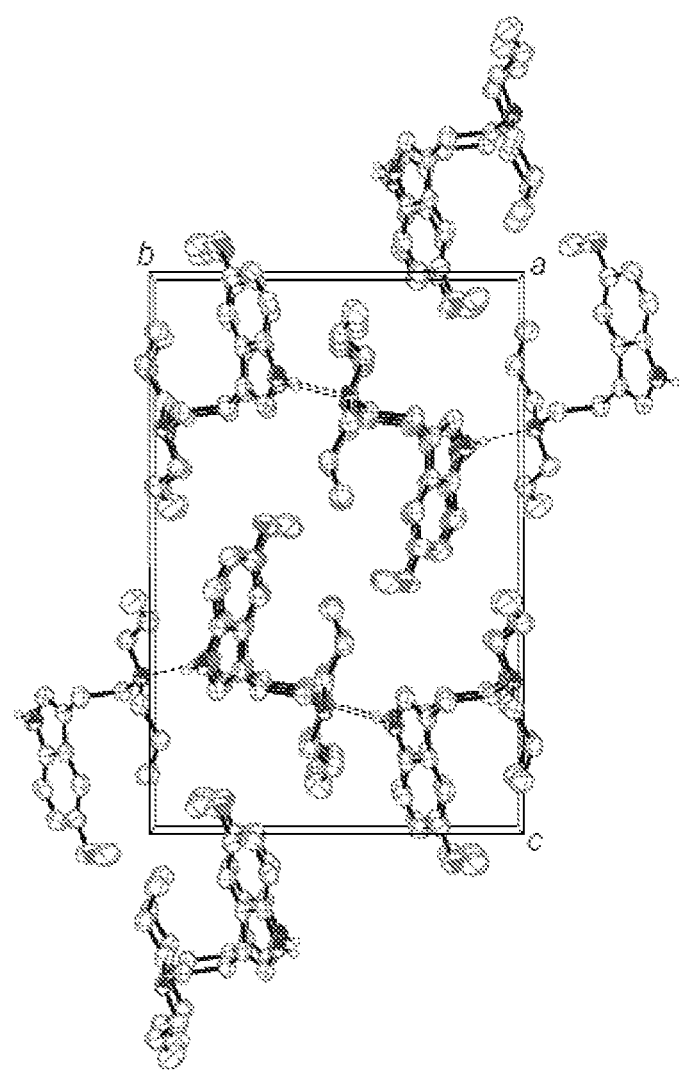
FIG. 2 shows the crystal packing of crystalline 5-MeO-DALT.

5-methoxy-N,N-diallyltryptamine has a single tryptamine molecule in the asymmetric unit. The asymmetric unit of 5-methoxy-N,N-diallyltryptamine contains a single tryptamine molecule shown in FIG. 1. The indole unit is near planar with a deviation from planarity of 0.015 Å. The methoxy group is in the same plane, with the indole and methoxy group showing an r.m.s. deviation of only 0.025 Å. The ethylamine group is turned significantly from the indole plane, with a C1-C8-C9-C10 torsion angle of 103.7 (2)°. The molecules are held together by an N1-H1 . . . N2 hydrogen bond between the indole N—H and the amino nitrogen. These hydrogen bonds join the molecules together along [010]. The crystal packing of 5-methoxy-N,N-diallyltryptamine, viewed along the a-axis is shown in FIG. 2. The N—H . . . N hydrogen bonds are shown as dashed lines.

Figure 3:
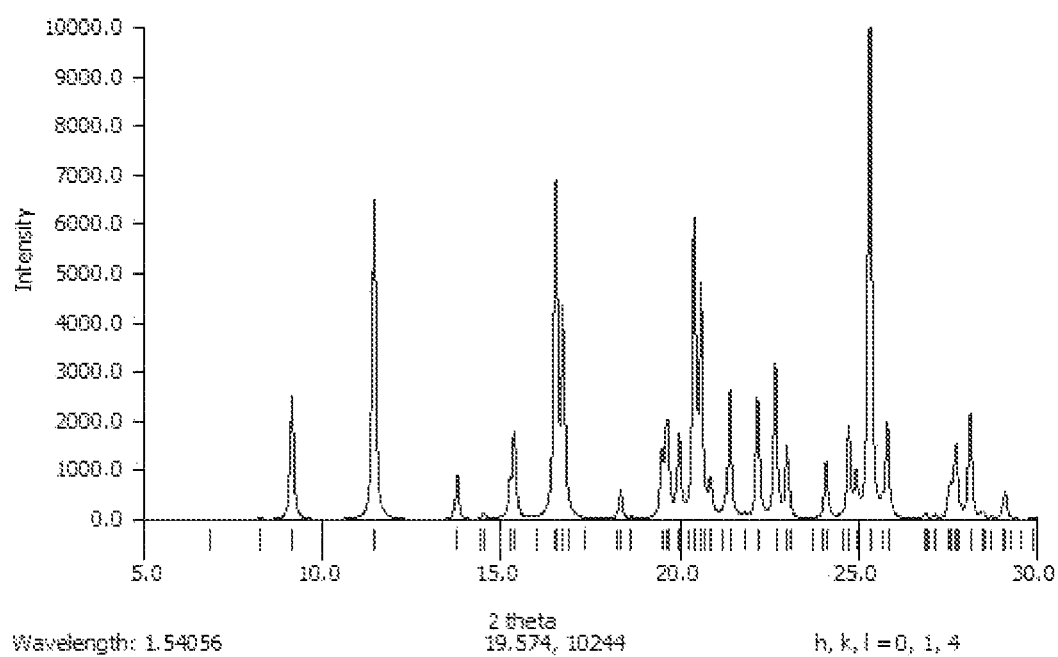
FIG. 3 shows a simulated x-ray power diffraction (XRPD) of crystalline 5-MeO-DALT.

FIG. 3 is a simulated x-ray powder diffraction (XRPD) of crystalline 5-MeO-DALT from its single crystal data. Crystalline 5-MeO-DALT may be characterized by the XRPD peaks at 9.1, 11.4, and 21.4° 2θ±0.2° 2θ as well as by an XRPD pattern substantially similar to FIG. 3.

Example 2: Synthesis and Crystallization of 5-MeO-DALT Fumarate

5-MeO-DALT fumarate was synthesized when 0.110 g of 5-MeO-DALT freebase was dissolved in 10 mL of methanol, and 47 mg of fumaric acid was added and refluxed overnight. 129 mg (82% yield) of white power was obtained upon removal of solvent in vacuo. The product was recrystallized in water to obtain single crystals suitable for X-ray diffraction. The product was analyzed by $^1$H NMR and $^{13}$C NMR.

$^1$H NMR (400 MHz, D$_2$O): δ 7.44 (d, J=8.8 Hz, 1H, ArH), 7.27 (s, 1H, ArH), 7.10 (d, J=2.3 Hz, 1H, ArH), 6.94 (dd, J=8.8, 2.4 Hz, 1H, ArH), 6.67 (s, 2H, CH), 5.91-5.81 (m, 2H, CH), 5.62-5.56 (m, 4H, CH$_2$), 3.87 (s, 3H, CH$_3$), 3.79 (d, J=7.2 Hz, 4H, CH$_2$), 3.42-3.38 (m, 2H, CH$_2$), 3.17-3.13 (m, 2H, CH$_2$).

$^{13}$C NMR (100 MHz, D$_2$O): δ 172.1 (COOH), 153.7 (CH), 135.3 (ArC), 132.5 (ArC), 127.22 (ArC), 127.20 (ArC), 126.2 (ArC), 125.8 (ArC), 113.7 (ArC), 112.6 (ArC), 108.9 (AkC), 101.3 (AkC), 56.8 (AkC), 55.7 (AkC), 52.2 (AkC), 20.4 (AkC).

Single crystal data, data collection and structure refinement details are summarized in Table 4.

TABLE 4

| | 5-MeO-DALT fumarate |
|---|---|
| Chemical formula | 0.25(C$_4$H$_2$O$_4$)•0.5(C$_{17}$H$_{23}$N$_2$O) |
| M$_r$ | 164.20 |
| Crystal system, space group | Triclinic, P$^-$1 |
| Temperature (K) | 297 |
| a, b, c (Å) | 7.8791 (7), 9.2908 (7), 13.5352 (11) |
| α, β, γ (°) | 108.081 (3), 104.365 (3), 95.903 (3) |
| V (Å$^3$) | 894.87 (13) |

TABLE 4-continued

| | 5-MeO-DALT fumarate |
|---|---|
| Z | 4 |
| F(000) | 352 |
| $D_x$ (Mg m$^{-3}$) | 1.219 |
| Radiation type | $M_o K_\alpha$ |
| $\lambda$ (Å) | 0.71073 |
| $\mu$ (mm$^{-1}$) | 0.08 |
| Crystal size (mm) | 0.34 × 0.28 × 0.22 |
| Diffractometer | Bruker D8 CMOS |
| Absorption correction | Multi-scan |
| | SADABS2016/2 (Bruker, 2016/2) was used for absorption correction. wR2(int) was 0.0533 before and 0.0481 after correction. The Ratio of minimum to maximum transmission is 0.9540. The $\lambda$/2 correction factor is Not present. |
| $T_{min}$, $T_{max}$ | 0.711, 0.745 |
| No. of measured, independent and observed [I > 2σ(I)] reflections | 27913, 3383, 2788 |
| $R_{int}$ | 0.035 |
| $\theta_{max}$, $\theta_{min}$ (°) | 25.7, 2.7 |
| $(\sin \theta/\lambda)_{max}$ (Å$^{-1}$) | 0.611 |
| R[F$^2$ > 2σ(F$^2$)], wR(F$^2$), S | 0.043, 0.114, 1.05 |
| w | $1/[\sigma^2(F_o^2) + (0.0485P)^2 + 0.266P]$ where $P = (F_o^2 + 2F_c^2)/3$ |
| No. of reflections | 3383 |
| No. of parameters | 226 |
| No. of restraints | 2 |
| h, k, l | −9→9, −11→11, −16→16 |
| H-site location | mixed |
| H-atom treatment | H atoms treated by a mixture of independent and constrained refinement |
| $(\Delta/\sigma)_{max}$ | 0.001 |
| $\Delta\rangle_{max}$, $\Delta\rangle_{min}$ (e Å$^{-3}$) | 0.26, −0.16 |

Computer programs: APEX3 (Bruker, 2018), SAINT (Bruker, 2018), SHELXT2014 (Sheldrick 2015a), SHELXL2018 (Sheldrick, 2015b), OLEX2 (Dolomanov et al., 2009), publCIF (Westrip, 2010).

Figure 4:
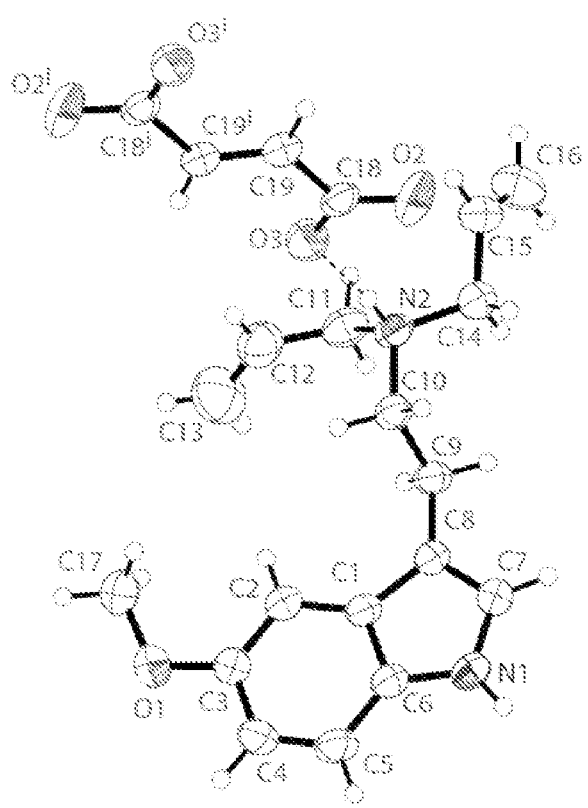
FIG. 4 shows the molecular structure of crystalline 5-MeO-DALT fumarate.

The molecular structure of crystalline 5-MeO-DALT fumarate, showing the atom labeling, is shown in FIG. 4. Hydrogen bonds are shown as dashed lines.

The asymmetric unit of 5-MeO-DALT fumarate contains one tryptammonium cation and one half of a fumarate dianion in the asymmetric unit. The tryptammonium and fumarate ions are held together in one-dimensional chains by a series of N—H . . . O hydrogen bonds. These chains are combinations of $R^4_4(22)$ rings, and $C^2_2(14)$ and $C^4_4(28)$ parallel chains along [111]. The cation possesses a near planar indole ring, with a mean deviation from planarity of 0.011 Å. The methoxy group is turned slightly away from this plane, with a C2-C3-O1-C17 torsion angle of 13.9 (3°). The ethyl-amino group is turned away from this plane, with a C7-C8-C9-C10 torsion angle of 103.9 (2°). The second half of the fumarate dianion is generated by inversion, and the dianion is near planar, with a mean deviation from planarity of 0.057 Å. The carboxylate unit is delocalized, with C—O distances of 1.271 (2) and 1.240 (2) Å.

Figure 5:
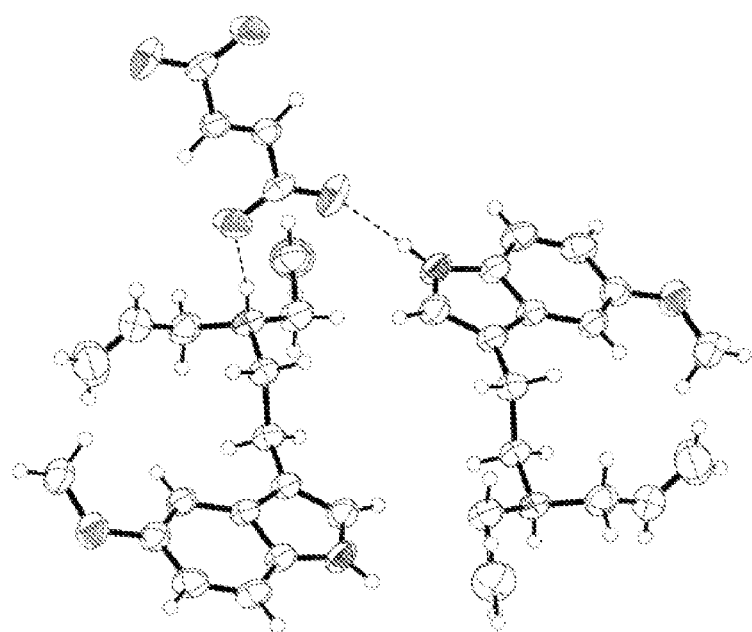
FIG. 5 shows the two to one ratio as a dimer of 5-MeO-DALT fumarate.

The two to one ratio as a dimer of 5-MeO-DALT fumarate is shown in FIG. 5.

Figure 6:
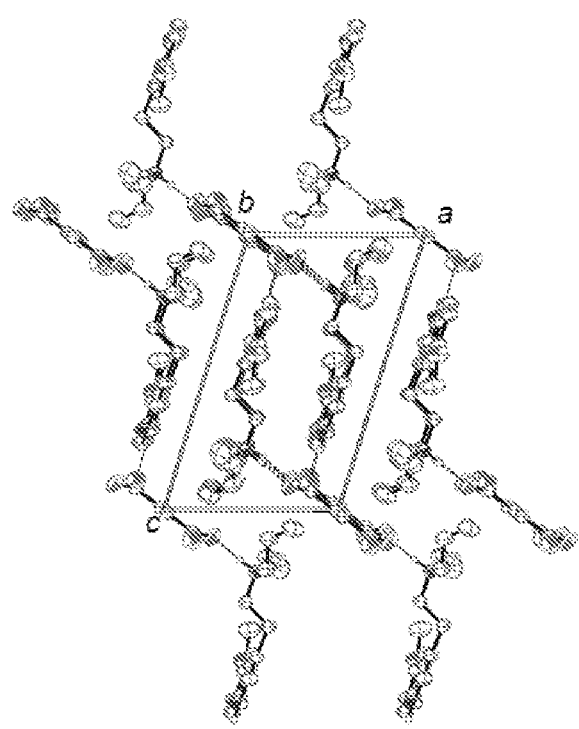
FIG. 6 shows the crystal packing of crystalline 5-MeO-DALT fumarate.

The crystal packing of 5-MeO-DALT fumarate, viewed along the b axis, is shown in FIG. 6. The N—H . . . O hydrogen bonds are shown as dashed lines.

Figure 7:
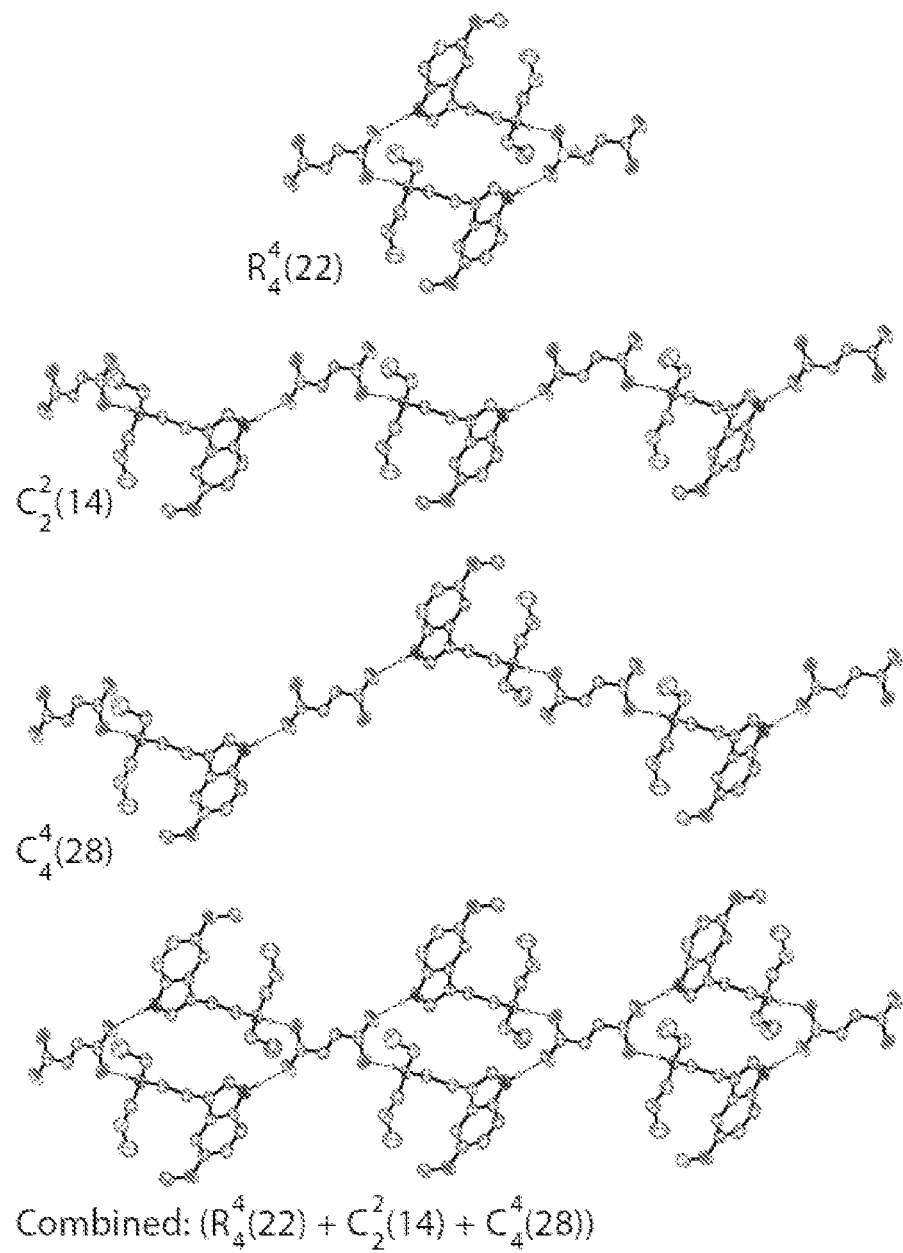
FIG. 7 shows the chains and rings of crystalline 5-MeO-DALT fumarate.

The tryptammonium cation and the fumarate dianion are linked together in the asymmetric unit through an N—H . . . O hydrogen bond between the ammonium nitrogen and a carboxylate oxygen. The indole nitrogen also exhibits an N—H . . . O hydrogen bond with another symmetry generated fumarate dianion. Two tryptammonium cations and two fumarate dianions are joined together through the N—H . . . O hydrogen bonds to form rings with graph-set notation $R^4_4(22)$ (Etter et al., 1990). The rings are joined together by two parallel chains along [111]. These chains have graph-set notation $C^2_2(14)$ and $C^4_4(28)$. The chains and rings of crystalline 5-MeO-DALT fumarate are shown in FIG. 7.

The hydrogen bonding network along [111], which consists of $R^4_4(22)$ rings that are joined together by two parallel $C^2_2(14)$ and $C^4_4(28)$ chains. The three components described in graph-set notation and the combined chain are shown in FIG. 7. Hydrogen bonds are shown as dashed lines.

Figure 8:
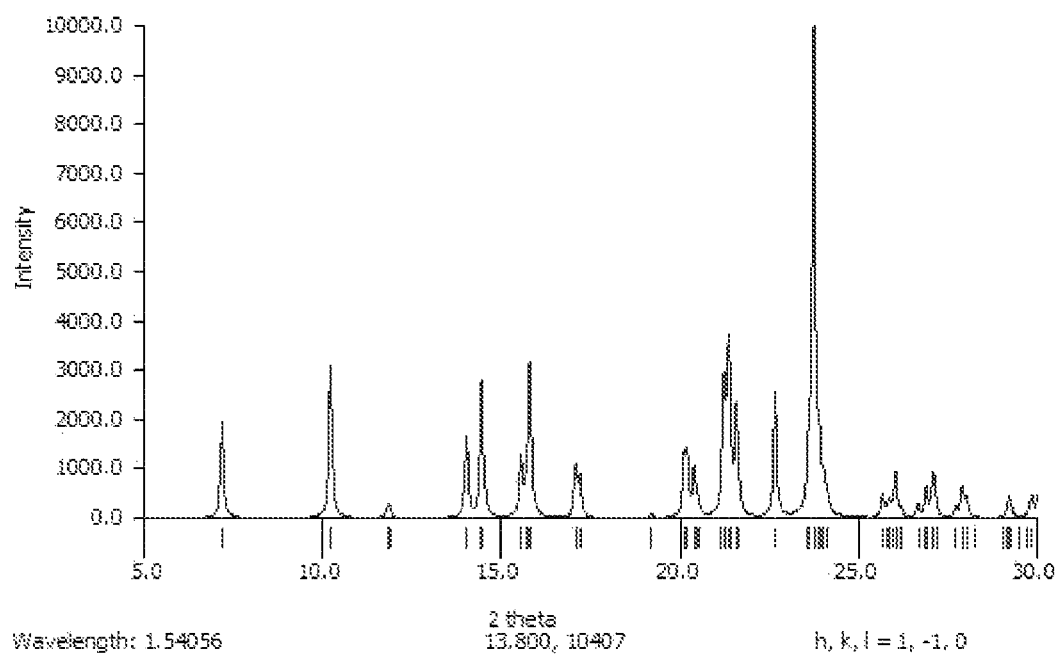
FIG. 8 shows a simulated x-ray power diffraction (XRPD) of crystalline 5-MeO-DALT fumarate.

FIG. 8 is a simulated x-ray powder diffraction (XRPD) of crystalline 5-MeO-DALT fumarate from its single crystal data. Crystalline 5-MeO-DALT fumarate may be characterized by the XRPD peaks at 7.2, 10.2, and 22.7° 2θ±0.2° 2θ as well as by an XRPD pattern substantially similar to FIG. 8.

REFERENCES

Bruker (2018). APEX3, SAINT, and SADABS. Bruker AXS Inc., Madison, Wisconsin, USA.

Carhart-Harris, R. L. & Goodwin, G. M. (2017). *Neuropsychopharmacology*, 42, 2105-2113.

Corkery, J. M., Durkin, E., Elliott, S., Schifano, F. & Ghodse, A. H. (2012). *Prog. Neuro-Psychoph.* 39, 259-262.

Cozzi, N. V. & Daley, P. F. (2016). *Bioorg. Med. Chem. Lett.* 26, 959-964.

Davis, A. K., Barrett, F. S. & Griffiths, R. R. (2020). *J. Contextual Behav. Sci.* 15, 39-45.

Dolomanov, O. V., Bourhis, L. J., Gildea, R. J., Howard, J. A. K. & Puschmann, H. (2009). *J. Appl. Cryst.* 42, 339-341.

Erspamer, V., Vitali, T., Roseghini, M. & Cei, J. M. (1967). *Biochem. Pharmacol.* 16, 1149-1164.

Etter, M. C., MacDonals, J. C. & Bernstein, J. (1990). Acta Cryst. B46, 256-262.

Sheldrick, G. M. (2015a). *Acta Cryst. A*71, 3-8.
Sheldrick, G. M. (2015b). *Acta Cryst.* C71, 3-8.
Sherwood, A. M., Claveau, R., Lancelotta, R., Kaylo, K. W. & Lenoch, K. (2020). *ACS Omega,* 5, 32067-32075.
Shulgin, A. T. & Shulgin, A. (2016). TiKHAL: The Continuation. Isomerdesign. Available at: http://isomerdesign.com/PiHKAL/read.php?domain=tk&id=56. Accessed 19 Mar. 2020.
Uthaug, M. V., Lancelotta, R., Szabo, A., Davis, A. K., Riba, J. & Ramaekers, J. G. (2019). *Psychpharmacology* 237, 773-785.
Uthaug, M. V., Lancelotta, R., van Oorsouw, K., Kuypers, K. P. C., Mason, N., Rak, J., Šuláková, A., Jurok, R., Maryška, M., Kuchař, M., Páleníček, T., Riba, J. & Ramaekers, J. G. (2019). *Psychopharmacology* 236, 2653-2666.
Weil, A. T. & Davis, W. (1994). *J. Ethnopharmacol.* 41, 1-8.

The claimed invention is:

1. A composition comprising crystalline 5-methoxy-N,N-diallyltryptamine (5-MeO-DALT) and an excipient.

2. A composition comprising a crystalline 5-methoxy-N,N-diallyltryptamine (5-MeO-DALT) and a second component selected from (a) a serotonergic drug, (b) a purified psilocybin derivative, (c) one or two purified cannabinoids and (d) a purified terpene.

3. Crystalline bis(5-meth-oxy-N,N-di-allyl-tryptammonium) fumarate (5-MeO-DALT fumarate).

4. A method of preventing or treating inflammation and/or pain comprising the step of:
administering to a subject in need thereof a therapeutically effective amount of crystalline 5-methoxy-N,N-diallyltryptamine (5-MeO-DALT).

5. A method of preventing or treating inflammation and/or pain comprising the step of:
administering to a subject in need thereof a therapeutically effective amount of a crystalline bis(5-meth-oxy-N,N-di-allyl-tryptammonium) fumarate (5-MeO-DALT fumarate) according to claim 3.

6. A method of preventing or treating inflammation and/or pain comprising the step of:
administering to a subject in need thereof a composition according to claim 1.

7. A method of preventing or treating inflammation and/or pain comprising the step of:
administering to a subject in need thereof a composition according to claim 2.

8. A method of preventing or treating inflammation and/or pain comprising the step of:
administering to a subject in need thereof a composition comprising crystalline bis(5-meth-oxy-N,N-di-allyl-tryptammonium) fumarate (5-MeO-DALT fumarate) according to claim 3 and an excipient.

9. A method of preventing or treating inflammation and/or pain comprising the step of:
administering to a subject in need thereof a composition comprising crystalline bis(5-meth-oxy-N,N-di-allyl-tryptammonium) fumarate (5-MeO-DALT fumarate) according to claim 3 and a second component selected from (a) a serotonergic drug, (b) a purified psilocybin derivative, (c) one or two purified cannabinoids and (d) a purified terpene.

10. A method of preventing or treating a brain disorder, the method comprising the step of:
administering to a subject in need thereof a therapeutically effective amount of crystalline 5-methoxy-N,N-diallyltryptamine (5-MeO-DALT).

11. A method of preventing or treating a brain disorder, the method comprising the step of:
administering to a subject in need thereof a composition according to claim 1.

12. A method of preventing or treating a brain disorder, the method comprising the step of:
administering to a subject in need thereof a composition according to claim 2.

13. The method of claim 10, wherein the brain disorder is selected from the group consisting of Huntington's disease, Alzheimer's disease, dementia, and Parkinson's disease.

14. A method of preventing or treating a disorder selected from the group consisting of: a developmental disorder; delirium; an amnestic disorder; a cognitive disorder; a psychiatric disorder due to a somatic condition; a drug-related disorder; a mood disorder; an anxiety disorder; a somatoform disorder; a factitious disorder; a dissociative disorder; an eating disorder; a sleep disorder; an impulse control disorder; an adjustment disorder; and a personality disorder, the method comprising the step of:
administering to a subject in need thereof a therapeutically effective amount of crystalline 5-methoxy-N,N-diallyltryptamine (5-MeO-DALT).

15. A method of preventing or treating a disorder selected from the group consisting of: a developmental disorder; delirium; an amnestic disorder; a cognitive disorder; a psychiatric disorder due to a somatic condition; a drug-related disorder; a mood disorder; an anxiety disorder; a somatoform disorder; a factitious disorder; a dissociative disorder; an eating disorder; a sleep disorder; an impulse control disorder; an adjustment disorder; and a personality disorder, the method comprising the step of:
administering to a subject in need thereof a composition according to claim 1.

16. A method of preventing or treating a disorder selected from the group consisting of: a developmental disorder; delirium; an amnestic disorder; a cognitive disorder; a psychiatric disorder due to a somatic condition; a drug-related disorder; a mood disorder; an anxiety disorder; a somatoform disorder; a factitious disorder; a dissociative disorder; an eating disorder; a sleep disorder; an impulse control disorder; an adjustment disorder; and a personality disorder, the method comprising the step of:
administering to a subject in need thereof a composition according to claim 2.

17. A method of preventing or treating a brain disorder, the method comprising the step of:
administering to a subject in need thereof a therapeutically effective amount of crystalline bis(5-meth-oxy-N,N-di-allyl-tryptammonium) fumarate (5-MeO-DALT fumarate) according to claim 3.

18. The method of claim 17, wherein the brain disorder is selected from the group consisting of Huntington's disease, Alzheimer's disease, dementia, and Parkinson's disease.

19. A method of preventing or treating a disorder selected from the group consisting of: a developmental disorder; delirium; an amnestic disorder; a cognitive disorder; a psychiatric disorder due to a somatic condition; a drug-related disorder; a mood disorder; an anxiety disorder; a somatoform disorder; a factitious disorder; a dissociative disorder; an eating disorder; a sleep disorder; an impulse control disorder; an adjustment disorder; and a personality disorder, the method comprising the step of:
administering to a subject in need thereof a therapeutically effective amount of crystalline bis(5-meth-oxy- N,N-di-allyl-tryptammonium) fumarate (5-MeO-DALT fumarate) according to claim 3.

* * * * *